United States Patent
Yakushiji (10) Patent No.: US 12,186,530 B2
(45) Date of Patent: Jan. 7, 2025

(54) LIQUID MEDICINE ADMINISTRATION DEVICE

(71) Applicant: TERUMO KABUSHIKI KAISHA, Tokyo (JP)

(72) Inventor: Yusuke Yakushiji, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 655 days.

(21) Appl. No.: 17/449,135

(22) Filed: Sep. 28, 2021

(65) Prior Publication Data

US 2022/0008648 A1 Jan. 13, 2022

Related U.S. Application Data (63) Continuation of application No. PCT/JP2020/007775, filed on Feb. 26, 2020.

(30) Foreign Application Priority Data

Mar. 29, 2019 (JP) .................. 2019-066288

(51) Int. Cl.
*A61M 5/145* (2006.01)
*A61M 5/142* (2006.01)
*A61M 5/172* (2006.01)

(52) U.S. Cl.
CPC .......... *A61M 5/1452* (2013.01); *A61M 5/172* (2013.01); *A61M 5/14248* (2013.01);
(Continued)

(58) Field of Classification Search
CPC ................ A61M 5/1452; A61M 5/172; A61M 2205/3306; A61M 2205/3365;
(Continued)

(56) References Cited

U.S. PATENT DOCUMENTS 9,320,849 B2 4/2016 Smith et al.
10,842,942 B2 * 11/2020 Iibuchi .............. A61M 5/31513
(Continued)

FOREIGN PATENT DOCUMENTS

CN 109067161 A 12/2018
JP 2001245975 A 9/2001
(Continued)

OTHER PUBLICATIONS

International Search Report (PCT/ISA/210) with English translation mailed on May 26, 2020, by the Japanese Patent Office as the International Searching Authority for International Application No. PCT/JP2020/007775.
(Continued)

*Primary Examiner* — Jason E Flick
*Assistant Examiner* — Adam J. Cermak
(74) *Attorney, Agent, or Firm* — BUCHANAN INGERSOLL & ROONEY PC (57) ABSTRACT

A liquid medicine administration device is configured to reduce the load on the power supply at the start of use and includes: a drive mechanism that advances a plunger that pushes a liquid medicine from a liquid medicine container filled with the liquid medicine toward a distal end opening of the liquid medicine container; and a control unit that controls operation of the drive mechanism, in which the drive mechanism includes a motor that applies, to the plunger, a drive force for advancing the plunger, and an encoder that detects a rotation of the motor, and when driving the drive mechanism, the control unit starts the encoder after starting the motor.

19 Claims, 6 Drawing Sheets

(52) U.S. Cl.
CPC ............ *A61M 2005/14506* (2013.01); *A61M 2205/3306* (2013.01); *A61M 2205/3365* (2013.01); *A61M 2205/8206* (2013.01); *F04B 2201/1201* (2013.01)

(58) Field of Classification Search
CPC .... A61M 2205/8206; F04B 2201/1201; F04B 2201/02011; G16H 20/13; G16H 20/17
See application file for complete search history.

(56) References Cited

U.S. PATENT DOCUMENTS

| | | |
|---|---|---|
| 2014/0228759 A1 | 8/2014 | Soma et al. |
| 2015/0025499 A1 | 1/2015 | Trock et al. |
| 2015/0320931 A1 | 11/2015 | Miyazawa |
| 2017/0037846 A1* | 2/2017 | Jeong .................... F04B 47/026 |
| 2017/0216524 A1* | 8/2017 | Haider ............... A61M 5/14248 |
| 2017/0284387 A1* | 10/2017 | Tomochika ........... F04B 49/103 |
| 2021/0340974 A1* | 11/2021 | Peng .................. F04B 45/0533 |

FOREIGN PATENT DOCUMENTS

| | | |
|---|---|---|
| JP | 2002-135974 A | 5/2002 |
| JP | 2003-088185 A | 3/2003 |
| JP | 2003-217793 A | 7/2003 |
| JP | 2004-215427 A | 7/2004 |
| JP | 2004-343892 A | 12/2004 |
| JP | 2014045859 A | 3/2014 |
| JP | 2015181869 A | 10/2015 |
| JP | 2018-182848 A | 11/2018 |
| WO | 2013/047855 A1 | 4/2013 |

OTHER PUBLICATIONS

The extended European Search Report issued Mar. 16, 2022, by the European Patent Office in corresponding European Patent Application No. 20782052.3-1122. (7 pages).

Office Action (Decision of Rejection) issued Sep. 1, 2023, by the National Intellectual Property Administration, P. R. China in corresponding Chinese Patent Application No. 202080021198.5 and an English translation of the Office Action. (12 pages).

* cited by examiner

TEMPORAL CHANGE IN POWER SUPPLY
VOLTAGE AT TIME OF START OF USE
(RELATED ART)

FIG. 11

TEMPORAL CHANGE IN POWER SUPPLY
VOLTAGE AT TIME OF START OF USE
(PRESENT APPLICATION)

LIQUID MEDICINE ADMINISTRATION DEVICE

CROSS-REFERENCES TO RELATED APPLICATIONS

This application is a continuation of International Patent Application No. PCT/JP2020/007775 filed on Feb. 26, 2020, which claims priority to Japanese Patent Application No. 2019-066288 filed on Mar. 29, 2019, the entire content of both of which is incorporated herein by reference.

FIELD OF THE INVENTION

The present invention relates to a liquid medicine administration device configured to reduce a load on a power supply at the start of use.

BACKGROUND DISCUSSION

In the related art, as disclosed in Japanese Patent Application Publication No. 2015-181869, there is known a syringe pump type liquid medicine administration device that administers a liquid medicine, filled in a liquid medicine container, to a living body. The syringe pump type liquid medicine administration device includes a power supply, a drive mechanism, and a control unit, and continuously administers the liquid medicine with high accuracy for a long time by moving a plunger little by little by the drive mechanism.

This type of liquid medicine administration device is refrigerated and stored until it is used by a user. Therefore, the liquid medicine administration device is devised to be extremely downsized so that a refrigerated storage space is small. For example, a power supply capacity is set to a minimum capacity capable of securing a capacity sufficient for normal administration of the liquid medicine after the refrigeration and storage in consideration of a decrease in the power supply capacity due to natural discharge during the refrigerated storage, and the power supply is configured by a button battery having a capacity sufficient to cover the set capacity.

SUMMARY

At the time of using the liquid medicine administration device, when a power switch is turned on, the control unit drives the drive mechanism simultaneously, and moves the plunger little by little to administer the liquid medicine to the living body. However, since a small button battery is adopted as the power supply, when a drive device is driven simultaneously, a load on the power supply increases, and a power supply voltage temporarily drops greatly. In the liquid medicine administration device, when the power supply voltage is smaller than a specified value, a safety device operates and all operations are stopped. Therefore, the administration of the liquid medicine is stopped.

The liquid medicine administration device disclosed here is configured to reduce a load on a power supply at the start of use.

The liquid medicine administration device including: a drive mechanism that advances a plunger that pushes a liquid medicine from a liquid medicine container filled with the liquid medicine toward a distal end opening of the liquid medicine container; and a control unit that controls operation of the drive mechanism, in which the drive mechanism includes a motor that applies, to the plunger, a drive force for advancing the plunger, and a rotation detection unit that detects a rotation of the motor, and when driving the drive mechanism, the control unit starts the rotation detection unit after starting the motor.

In the liquid medicine administration device, since the rotation detection unit is started after the motor is started, the load on the power supply at the start of use can be reduced.

In accordance with another aspect, a liquid medicine administration device comprises: a housing; a liquid medicine container that possesses a distal end, the liquid medicine container containing liquid medicine, with the distal end of the liquid medicine container including an opening through which the liquid medicine in the liquid medicine container is discharged during administration of the liquid medicine; an axially movable plunger connected to a gasket that is slidably positioned in the liquid medicine container so that axial movement of the plunger toward the distal end of the liquid medicine container results in axial movement of the gasket towards the liquid medicine of the liquid medicine container and discharge of the liquid medicine through the opening at the distal end of the liquid medicine container; a motor operatively connected to the plunger to axially move the plunger and the gasket toward the distal end of the liquid medicine container; and a rotation detector that detects rotation of the motor. A control unit is connected to the motor and to the rotation detector to control operation of the motor and the rotation detector, including starting operation of the motor and starting operation of the rotation detector. The control unit is configured to start operation of the rotation sensor after the operation of the motor has been started and after the motor has been operating.

According to another aspect, a method comprises inserting a needle tube into a living body, wherein the needle tube is connected to an opening at a distal end of a liquid medicine container containing liquid medicine, with a gasket positioned in the liquid medicine container and connected to a plunger so that axial movement of the plunger results in axial movement of the gasket. The plunger is operatively connected to a motor so that operation of the motor results in the axial movement of the plunger and the gasket, with the motor rotating during operation, and rotation of the motor being detected by a rotation detector. The method additionally involves starting operation of the motor, operating the motor so that the motor rotates and axially moves the plunger and the gasket toward the distal end of the liquid medicine container to discharge the liquid medicine through the opening at the distal end of the liquid medicine and is delivered to the needle tube so that the liquid medicine is administered to the living body, and starting operation of the rotation detector after the motor is operating.

DETAILED DESCRIPTION

Set forth below with reference to the accompanying drawings is a detailed description of embodiments of a liquid medicine administration system, a liquid medicine administration device and an administration tool representing examples of the inventive liquid medicine administration system, liquid medicine administration device and administration tool disclosed here. The following description does not limit the technical scope or meaning of terms in the claims. Furthermore, dimensional ratios in the drawings are exaggerated for convenience of description, and may be different from actual ratios.

Figure 1:
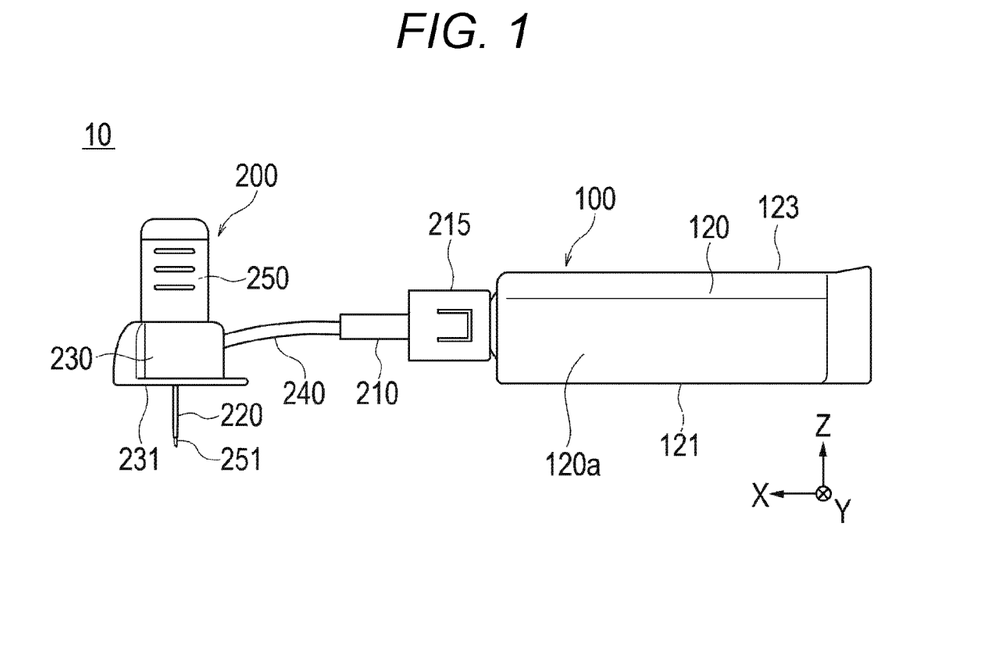
FIG. 1 is a side view of a liquid medicine administration system.
Figure 2:
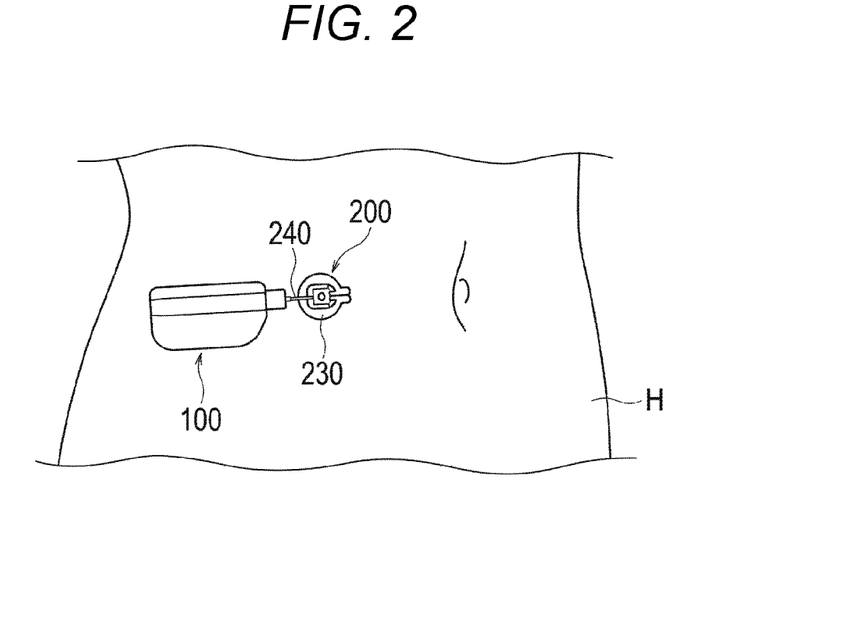
FIG. 2 is a view schematically illustrating a usage example of a liquid medicine administration system.
Figure 3:
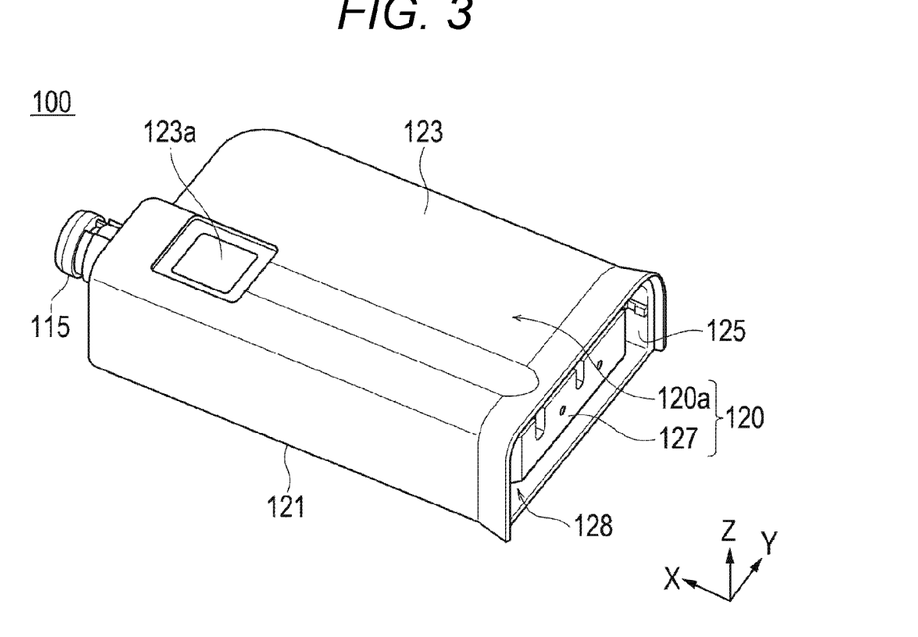
FIG. 3 is a schematic perspective view of a liquid medicine administration device.
Figure 4:
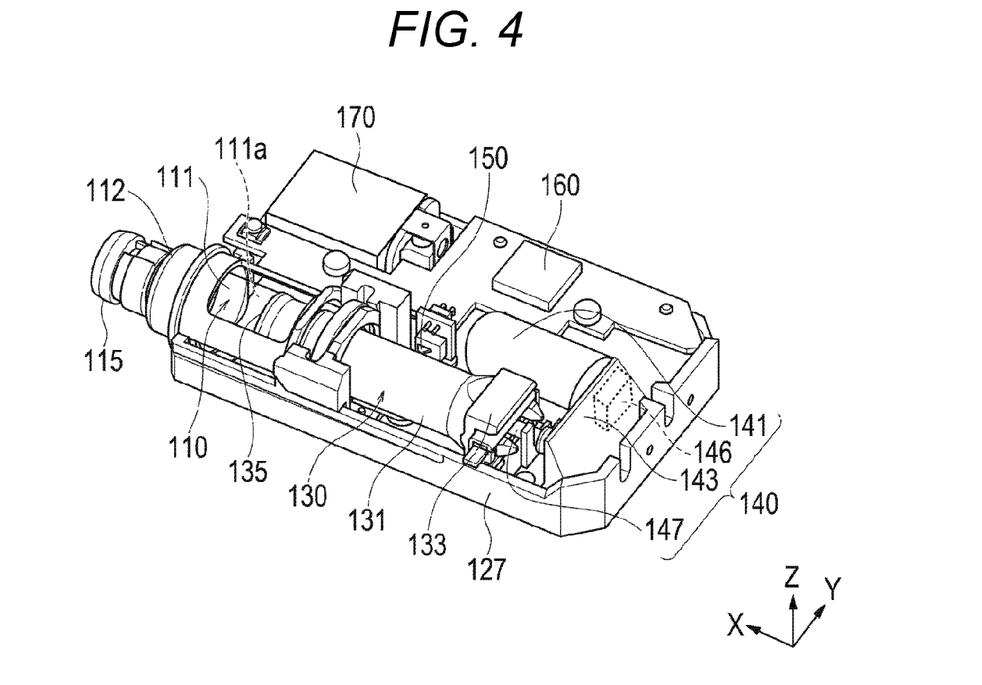
FIG. 4 is a schematic perspective view of a chassis included in a housing and each component member assembled to the chassis.
Figure 5:
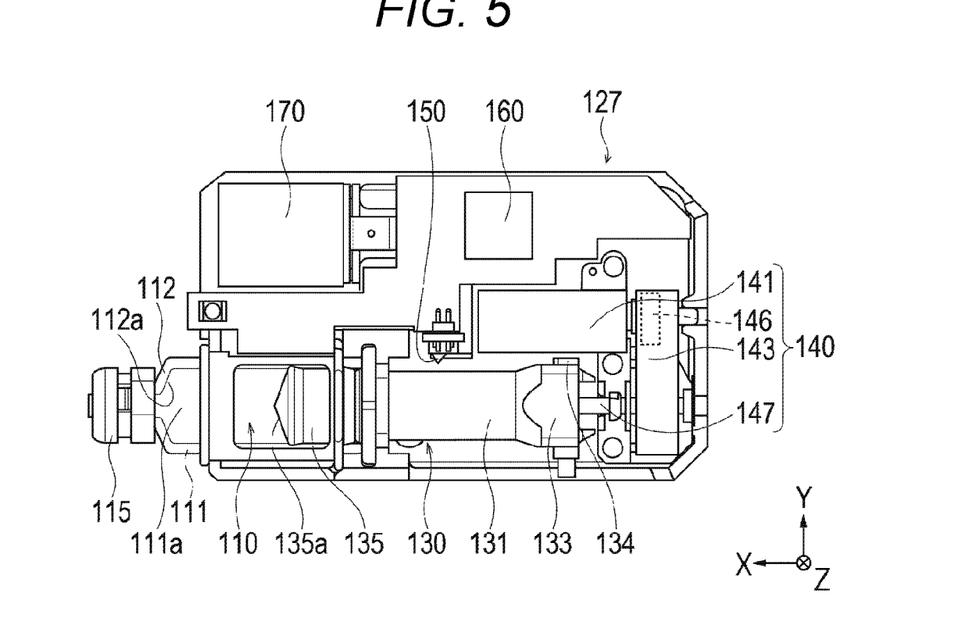
FIG. 5 is a plan view of a liquid medicine administration device illustrating a state before a plunger is moved forward.
Figure 6:
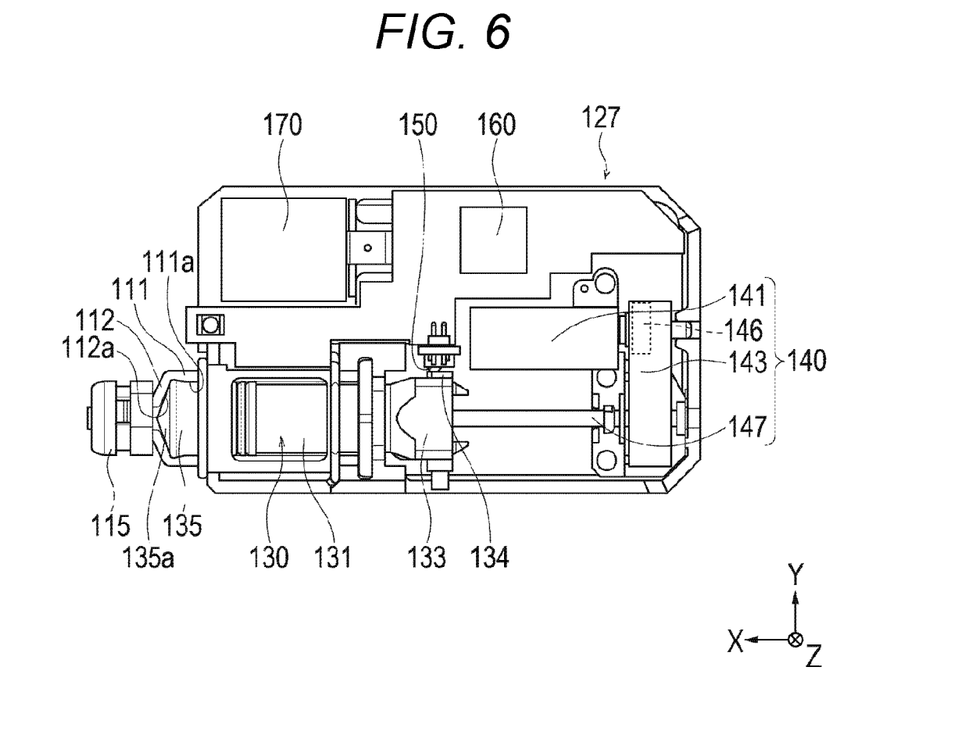
FIG. 6 is a plan view of a liquid medicine administration device illustrating a state after the plunger is moved forward.

FIGS. 1 to 6 illustrate a liquid medicine administration system 10, a liquid medicine administration device 100, and an administration tool 200 according to the present embodiment. FIG. 1 is a side view of a liquid medicine administration system. FIG. 2 is a view schematically illustrating a usage example of the liquid medicine administration system. FIG. 3 is a schematic perspective view of a liquid medicine administration device. FIG. 4 is a schematic perspective view of a chassis included in a housing and each component member assembled to the chassis. FIG. 5 is a plan view of the liquid medicine administration device illustrating a state before a plunger is moved forward. FIG. 6 is a plan view of the liquid medicine administration device illustrating a state after the plunger is moved forward. An arrow X in each drawing indicates a "longitudinal direction (longitudinal direction of a liquid medicine container 110)" of the liquid medicine administration device 100, an arrow Y indicates a "width direction (depth direction)" of the liquid medicine administration device 100, and an arrow Z indicates a "height direction" of the liquid medicine administration device 100.

Liquid Medicine Administration System

The liquid medicine administration system 10 is used to administer a liquid medicine into a living body. As illustrated in FIG. 1, the liquid medicine administration system 10 includes the liquid medicine administration device 100 and the administration tool 200.

As illustrated in FIG. 2, the liquid medicine administration device 100 and the administration tool 200 are configured as a patch type used by being stuck on a body surface (skin) H of a user. A body part of the user to which the liquid medicine administration device 100 and the administration tool 200 are attached is not particularly limited, but is, for example, an abdomen or a femoral part.

For example, the liquid medicine administration system 10 can continuously administer a liquid medicine filled in the liquid medicine container 110 included in the liquid medicine administration device 100 into the living body for a relatively long time (for example, approximately several minutes to several hours) by a pressing action of a plunger 130 (see FIG. 4) to be described later. The liquid medicine administration system 10 may be configured to intermittently administer the liquid medicine into the living body.

Liquid Medicine Administration Device

As illustrated in FIGS. 3 to 6, the liquid medicine administration device 100 includes the liquid medicine container 110 including a cylindrical (barrel-shaped) main body 111 filled with the liquid medicine, a housing 120 that holds the liquid medicine container 110, the plunger 130 that pushes the liquid medicine in the liquid medicine container 110, a drive mechanism 140 that advances (axially advances) the plunger 130 toward a distal end opening of the liquid medicine container 110, a detection unit 150 that detects a portion 134 to be detected of the plunger 130 and detects completion of feeding of the liquid medicine based on a detection result, and a control unit 160 that controls operation of the drive mechanism.

As illustrated in FIGS. 3 and 4, the housing 120 includes a box-shaped housing main body 120a in which an accommodation space 128 is formed, and a chassis (corresponding to a "support portion") 127 which is accommodated in the accommodation space 128 of the housing main body 120a and can be fixed to the housing main body 120a.

As illustrated in FIG. 3, a window portion 123a that allows the inside of the accommodation space 128 to be visually recognized from the outside of the housing 120 is formed on an upper surface 123 of the housing main body 120a. The window portion 123a is formed by providing a transparent or translucent portion in a part of the housing main body 120a.

A proximal end opening 125 for inserting a chassis 127 into the accommodation space 128 of the housing main body 120a is formed on a proximal end side in a longitudinal direction of the housing main body 120a. The proximal end opening 125 of the housing main body 120a is closed by a lid member in a state in which the chassis 127 is accommodated in the accommodation space 128.

A bottom surface 121 of the housing main body 120a is provided with a sheet-like sticking portion that can be stuck to the body surface H of the user. In an initial state before the liquid medicine administration device 100 is attached to the user, a peelable or removable protective sheet is attached to a sticking surface of the sticking portion.

As illustrated in FIG. 4, the chassis 127 holds the liquid medicine container 110, the plunger 130, the drive mechanism 140, the detection unit 150, the control unit 160, and a power supply unit 170.

The liquid medicine container 110 is a so-called prefilled liquid medicine container. Therefore, the liquid medicine is filled in a lumen 111a of the main body 111 of the liquid medicine container 110 in advance. Examples of the liquid medicine include protein preparations, narcotic analgesics, diuretics, and the like.

A sealing member for preventing leakage of the liquid medicine is disposed in the distal end opening (discharge port) formed at a distal end 112 of the liquid medicine container 110. As illustrated in FIG. 3, the distal end opening of the liquid medicine container 110 is disposed so as to protrude outward from the housing main body 120a. Furthermore, an attachment portion 115 that is connected to a tube 240 (see FIG. 1) to be described later is attached to a distal end portion of the liquid medicine container 110, the distal end portion protruding from the housing main body 120a.

A main body 131 of the plunger 130 is inserted into or positioned in the lumen 111a of the main body 111 of the liquid medicine container 110 (see FIGS. 4 and 5). A gasket 135 slidable on an inner wall of the liquid medicine container 110 is disposed at a distal end of the main body 131 of the plunger 130. The gasket 135 liquid-tightly seals a proximal end side of the gasket 135 by liquid-tightly bringing an outer circumferential portion of the gasket 135 into close contact with an inner circumferential surface of the main body 111 of the liquid medicine container 110.

In the present embodiment, the gasket 135 is configured to be shrinkable in a direction (longitudinal direction) in which the plunger 130 advances when the plunger 130 advances in a state in which the gasket 135 abuts against a distal end inner wall 112a (see FIG. 5) of the liquid medicine container 110. The gasket 135 can be made of, for example, a flexible resin material such as a rubber material or an elastomer so as to be shrinkable as described above.

As illustrated in FIG. 5, the gasket 135 has a tapered shape in which an outer diameter decreases toward a distal end side. Furthermore, the shape of the gasket 135 is substantially the same as the shape of the distal end inner wall 112a of the liquid medicine container 110.

As illustrated in FIG. 5, the portion 134 to be detected is provided at a proximal end of the plunger 130. The portion 134 to be detected is used to detect completion of feeding of the liquid medicine by the liquid medicine administration device 100.

The control unit 160 controls a liquid medicine feeding operation of the liquid medicine administration device 100. The control unit 160 can be configured by, for example, a known microcomputer (electronic circuit element) on which a CPU, a RAM, a ROM, and the like are mounted. The control unit 160 integrally controls operations of the drive mechanism 140, the detection unit 150, and the power supply unit 170.

As illustrated in FIG. 5, the detection unit 150 is disposed in the chassis 127. As illustrated in FIG. 6, the detection unit 150 detects completion of feeding of the liquid medicine of the liquid medicine administration device 100 when the portion 134 to be detected included in the plunger 130 comes into contact with the detection unit 150. The detection unit 150 can be configured by, for example, a known contact-type sensor that transmits a predetermined electric signal when the portion 134 to be detected comes into contact with the detection unit 150. The control unit 160 acquires information regarding completion of feeding of the liquid medicine by receiving the electric signal from the detection unit 150. When the plunger 130 advances by a predetermined amount, the specific configuration and the like of the detection unit 150 are not particularly limited as long as a position of the portion 134 to be detected of the plunger 130 can be detected.

The power supply unit 170 can be configured by, for example, a known button battery or the like. The liquid medicine administration device 100 is required to be downsized. Therefore, a small button battery is used as the power supply unit 170.

As illustrated in FIG. 4, the drive mechanism 140 includes a motor 141 that receives a drive current from the power supply unit 170 and applies a drive force, a speed reduction mechanism 143 that includes a gear or the like transmitting the drive force of the motor 141, an encoder 146 that is provided adjacent to the speed reduction mechanism 143 and includes a photointerrupter as a rotation detection unit that detects rotation of the motor 141 and a slit plate that rotates in accordance with the rotation of the motor 141, and a feed screw 147 that is connected to the speed reduction mechanism 143.

The feed screw 147 is connected to a proximal end connection portion 133 disposed in the vicinity of the proximal end of the plunger 130. The feed screw 147 converts a rotational motion transmitted from the speed reduction mechanism 143 into a linear motion to advance the plunger 130 in the longitudinal direction (X direction). The plunger 130 advances toward a distal end side of the liquid medicine container 110 to push the liquid medicine from the lumen 111a of the main body 111 of the liquid medicine container 110 to the tube 240 (see FIG. 1).

Administration Tool

As illustrated in FIGS. 1 and 2, the administration tool 200 is configured to be connectable to the liquid medicine administration device 100.

The administration tool 200 includes a connector 210, a needle tube 220 that punctures the living body, a puncture unit (cannula housing) 230, the tube 240, and a puncture assisting tool 250 that assists in puncturing the living body with the needle tube 220.

The connector 210 is configured to be connectable to the liquid medicine administration device 100 via an attachment portion 215 fixed to the connector 210. The attachment portion 215 can be connected to the liquid medicine administration device 100 by being externally fitted to the attachment portion 115 (see FIG. 4) provided in the vicinity of the distal end 112 of the liquid medicine container 110 protruding to the outside of the housing 120.

Inside the attachment portion 215, a connection needle portion through which the sealing member disposed at a distal end portion of the liquid medicine container 110 can be inserted is disposed. The tube 240 communicates with the lumen 111a of the main body 111 of the liquid medicine container 110 via the connection needle portion.

Inside the puncture unit 230, a flow path through which the tube 240 communicates with a lumen of the needle tube 220 is formed. The liquid medicine fed to the puncture unit 230 through the tube 240 is administered into the living body through the flow path formed inside the puncture unit 230 and the needle tube 220.

When the liquid medicine is fed to the user, the puncture assisting tool 250 is attached to the puncture unit 230. The puncture assisting tool 250 holds an introduction needle (inner needle) 251. The introduction needle 251 protrudes from a distal end of the needle tube 220 in a state in which the puncture assisting tool 250 is attached to the puncture unit 230. By puncturing the living body with the needle tube 220 in a state in which the introduction needle 251 is inserted into the needle tube 220, the user can insert the needle tube 220 into the living body while preventing the needle tube 220 from being broken or the like.

The puncture assisting tool 250 is removed from the puncture unit 230 after puncturing the living body with the needle tube 220. When the puncture assisting tool 250 is removed from the puncture unit 230, the introduction needle 251 is removed from the lumen of the needle tube 220.

After puncturing the living body with the needle tube 220, the puncture assisting tool 250 is removed, and the puncture unit 230 is left on the body surface H of the user in a state in which the needle tube 220 is indwelled in the living body. When the plunger 130 of the liquid medicine administration device 100 advances in the liquid medicine container 110 in this state, the liquid medicine filled in the liquid medicine container 110 is fed to the lumen of the needle tube 220 via the tube 240 and the flow path of the puncture unit 230.

The introduction needle 251 can be formed of, for example, a metal needle. Furthermore, the needle tube 220 can be formed of, for example, a resin tubular member (cannula).

Similarly to the liquid medicine administration device 100, the administration tool 200 is configured as a patch type used by being stuck on the body surface H of the user. A sheet-like sticking portion that can be stuck to the body surface H is provided on a contact surface (bottom surface) 231 of the puncture unit 230 of the administration tool 200. In an initial state before the administration tool 200 is attached to the user, a peelable protective sheet is attached to a sticking surface of the sticking portion.

As described above, a schematic configuration of the liquid medicine administration system 10, the liquid medicine administration device 100, and the administration tool 200 has been described. The liquid medicine administration device 100 is required to be reduced in size and cost in order to facilitate handling at the time of use and to save a storage space at the time of storage. Therefore, a small button battery is adopted as the power supply unit 170. Since there is a limit to supplying large electric power instantaneously, the button battery cannot apply a large load at a time. Therefore, the control unit 160 controls the drive mechanism 140 as follows.

Figure 7A:
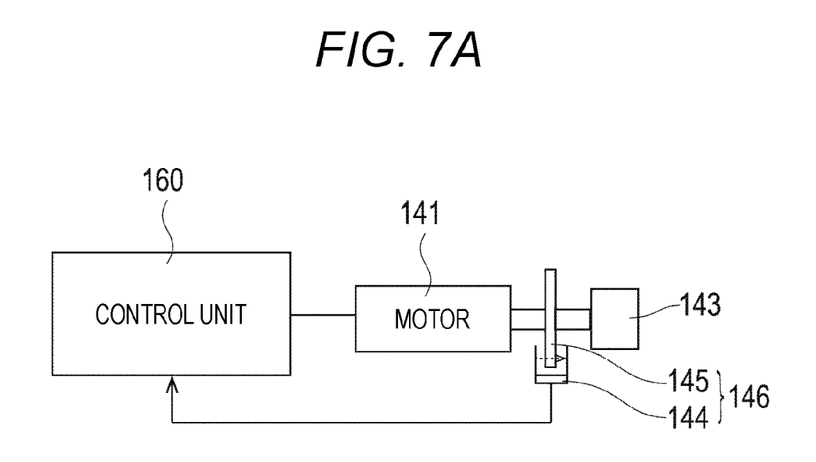
FIG. 7A is a block diagram of a control system of a liquid medicine administration device.
Figure 7B:
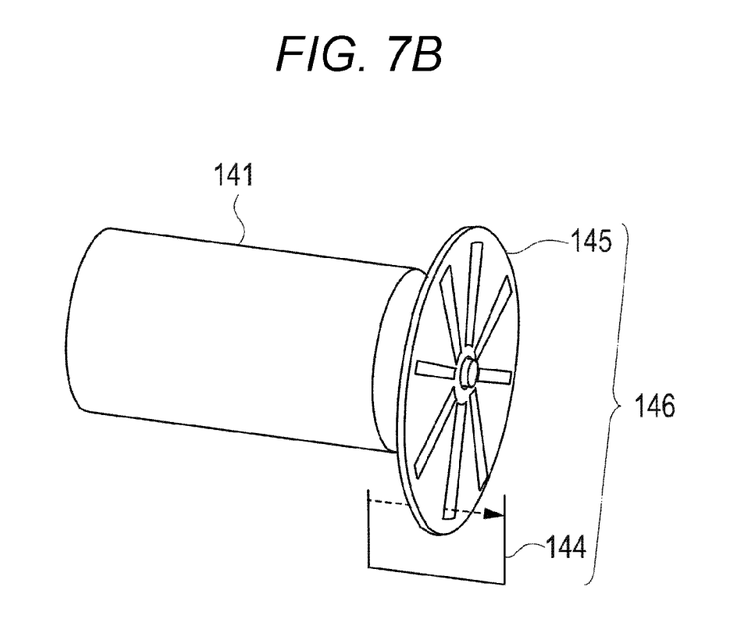
FIG. 7B is a diagram schematically illustrating a configuration of an encoder of FIG. 7A.
Figure 8:
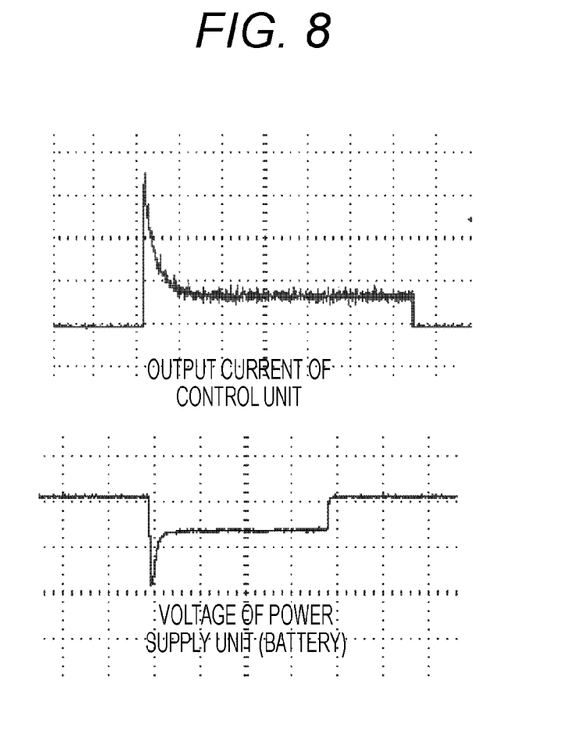
FIG. 8 is a graph illustrating temporal changes in an output current and a power supply voltage of a control unit at the start of use.
Figure 9:
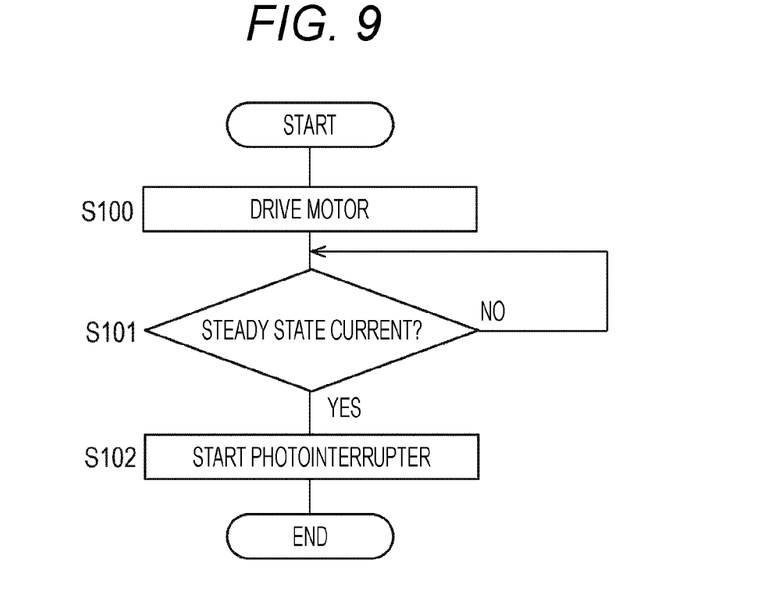
FIG. 9 is an operation flowchart of a control unit.
Figure 10:
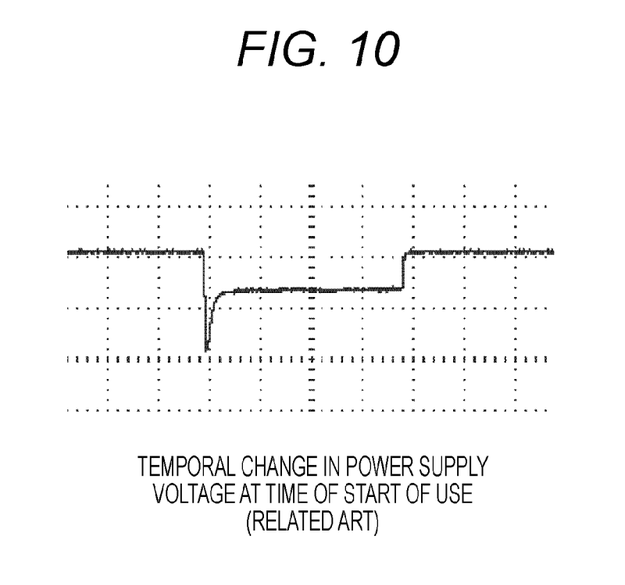
FIG. 10 is a diagram illustrating a temporal change in a power supply voltage of the related art at the start of use of a liquid medicine administration device.
Figure 11:
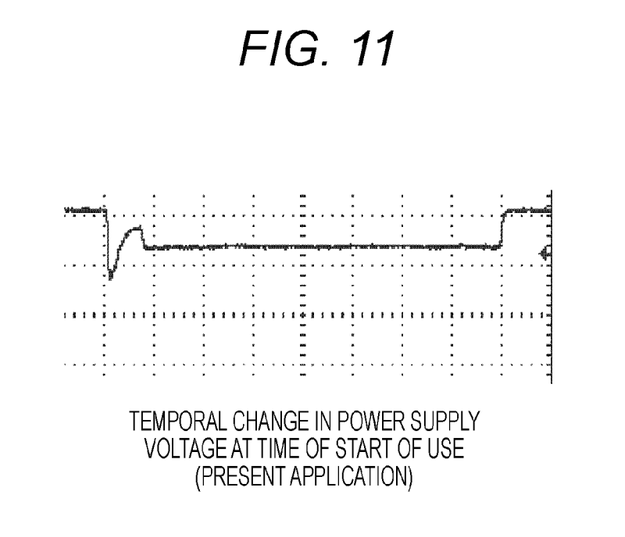
FIG. 11 is a diagram illustrating a temporal change in a power supply voltage of the present application at the start of using a liquid medicine administration device.

Next, a specific operation of the control unit 160 will be described with reference to FIGS. 7A to 11. FIG. 7A is a block diagram of a control system of the liquid medicine administration device 100. FIG. 7B is a diagram schematically illustrating a configuration of the encoder of FIG. 7A. FIG. 8 is a graph illustrating temporal changes in an output current and a power supply voltage of the control unit 160 at the start of use. FIG. 9 is an operation flowchart of the control unit 160. FIG. 10 is a diagram illustrating a temporal change in a power supply voltage of the related art at the start of using the liquid medicine administration device 100. FIG. 11 is a diagram illustrating a temporal change in a power supply voltage of the present application at the start of using the liquid medicine administration device 100.

As illustrated in FIG. 7A, the control unit 160 is electrically connected to the motor 141. A rotation shaft of the motor 141 is mechanically connected to the encoder 146 as the rotation detection unit and the speed reduction mechanism 143. As also illustrated in FIG. 7B, the encoder 146 includes a photointerrupter 144 including an optical sensor and a slit plate 145 in which a large number of slits are radially formed, and detects the rotation of the motor 141 by detecting whether or not light passes through the slits of the slit plate 145 with the optical sensor of the photointerrupter 144. As illustrated in FIG. 7A, the photointerrupter 144 is electrically connected to the control unit 160. The present embodiment describes that the encoder 146 may use the photointerrupter 144 as the rotation detection unit, but this is one example and an encoder using a magnetic sensor may alternatively be used.

When the control unit 160 rotates the motor 141, the speed reduction mechanism 143 is driven, and the plunger 130 advances in the liquid medicine container 110 (see FIGS. 5 and 6). The encoder 146 provided adjacent to the speed reduction mechanism 143 detects the rotation of the motor (e.g., rotation of the motor output) 141, and the control unit 160 calculates a rotation speed of the motor 141 based on the rotation of the motor 141 detected by the encoder 146. The rotation of the motor 141 detected by the encoder 146 is fed back to the control unit 160, and the control unit 160 calculates the rotation speed of the motor 141 in accordance with the feedback and determines whether or not the motor 141 is rotating. The rotation detection unit can also be incorporated as a part of the speed reduction mechanism 143. Specifically, the slit plate 145 is omitted, and instead of this, a large number of slits are radially provided in the gear of the speed reduction mechanism 143, and the rotation of the motor 141 is detected by detecting whether or not light passes through the slits provided in the gear by using the optical sensor of the photointerrupter. In this case, the encoder includes the gear of the speed reduction mechanism 143 and the photointerrupter.

At the start of using the liquid medicine administration device 100, as illustrated in an upper graph of FIG. 8, a momentarily excessively large current (starting current that forms a peak current) flows, after that, the current decreases to a steady state current in response to the magnitude of the load, and is stabilized. As illustrated in a lower graph of FIG. 8, a voltage of the button battery which is the power supply unit 170 decreases momentarily excessively in response to the magnitude of the flowing current, and then the decrease in the voltage is stabilized. When the voltage of the button battery is too low, all the operations of the liquid medicine administration device 100 are stopped, and the administration of the medicine is interrupted.

Therefore, as illustrated in an operation flowchart of FIG. 9, the control unit 160 first drives the motor 141 (S100), and when the current of the motor 141 decreases to a steady state current in response to the load (S101), starts the photointerrupter 144 (S102).

That is, at the start of using the liquid medicine administration device 100, the control unit 160 first drives the motor 141, and starts the photointerrupter 144 after the current of the motor 141 is stabilized, so that the starting currents of the motor 141 and the photointerrupter 144 are not supplied from the power supply unit 170 at a time (at the same initial time). Thus, the start of the operation of the photointerrupter 144 is delayed relative to the start of operation of the motor 141 so that the motor 141 operates for a period of time before operation of the photointerrupter 144 is started.

In the related art (known art), since the motor 141 and the photointerrupter 144 are started at the same timing at the start of using the liquid medicine administration device 100, as illustrated in FIG. 10, the power supply voltage drops greatly and so the safety device of the liquid medicine administration device 100 is readily operated. However, as in the present application, when the photointerrupter 144 is started after the motor 141 is started, as illustrated in FIG. 11, the voltage temporarily drops twice, but the power supply voltage does not drop greatly (i.e., does not drop so significantly) as in the related art, and so the safety device is difficult to be operated (i.e., is not so likely to be operated). That is, the administration of the liquid medicine is not interrupted.

Therefore, the load on the power supply unit 170 at the start of using the liquid medicine administration device 100 can be reduced. According to this, a battery constituting the power supply unit 170 can last longer than the related art. Furthermore, even in a case where the voltage of the battery decreases or internal resistance of the battery increases, the operation range of the battery can be expanded. Furthermore, since electric capacity of the power supply unit 170 can be reduced, miniaturization and cost reduction of the liquid medicine administration device 100 can be achieved.

The detailed description above describes embodiments of a liquid medicine administration device and operational method representing examples of the inventive liquid medicine administration device and operational method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A liquid medicine administration device comprising:
  a housing;
  a liquid medicine container that possesses a distal end, the liquid medicine container containing liquid medicine, the distal end of the liquid medicine container including an opening through which the liquid medicine in the liquid medicine container is discharged during administration of the liquid medicine;
  an axially movable plunger connected to a gasket that is slidably positioned in the liquid medicine container so that axial movement of the plunger toward the distal end of the liquid medicine container results in axial movement of the gasket towards the liquid medicine of the liquid medicine container and discharge of the liquid medicine through the opening at the distal end of the liquid medicine container;
  a motor operatively connected to the plunger to axially move the plunger and the gasket toward the distal end of the liquid medicine container;
  a rotation detection unit that detects rotation of the motor;
  a control unit connected to the motor and to the rotation detection unit to control operation of the motor and the rotation detection unit, including starting the motor and starting the rotation detection unit; and
  the control unit being configured to start the motor and to start the rotation detection unit at different times so that the rotation detection unit is started after the motor has been started and after the motor has been operating.

2. The liquid medicine administration device according to claim 1, wherein the control unit is configured to start the rotation detection unit after current supplied to the motor is stabilized.

3. The liquid medicine administration device according to claim 2, wherein the rotation detection unit is an encoder including a photointerrupter.

4. The liquid medicine administration device according to claim 1, wherein the rotation detection unit is an encoder including a photointerrupter.

5. The liquid medicine administration device according to claim 1, wherein the motor, the liquid medicine container and the plunger are housed in the housing.

6. The liquid medicine administration device according to claim 5, further comprising an attachment portion attached to a distal end portion of the liquid medicine container and protruding outside the housing in a direction away from the housing, the attachment portion being configured to be connected to a tube of an administration tool that is used to administer the liquid medicine to a living body.

7. The liquid medicine administration device according to claim 5, further comprising a battery positioned in the housing and connected to the motor to supply drive current to the motor.

8. A liquid medicine administration device comprising:
  a drive mechanism that, when supplied with current, operates to advance a plunger to push liquid medicine from a liquid medicine container filled with the liquid medicine toward a distal end opening of the liquid medicine container;
  a control unit configured to control operation of the drive mechanism;
  the drive mechanism including a motor that, when supplied with the current, operates to apply a drive force to the plunger for advancing the plunger, and a rotation detection unit that, when supplied with the current, operates to detect rotation of the motor; and
  the control unit being configured to begin supplying the current to the motor and to begin supplying the current to the rotation detection unit at different times so that the control unit starts the rotation detection unit after the control unit starts the motor.

9. The liquid medicine administration device according to claim 8, wherein
  the control unit is configured to start the motor and to then, after the current supplied to the motor is stabilized, start the rotation detection unit.

10. The liquid medicine administration device according to claim 9, wherein the rotation detection unit is an encoder including a photointerrupter.

11. The liquid medicine administration device according to claim 8, wherein the rotation detection unit is an encoder including a photointerrupter.

12. The liquid medicine administration device according to claim 8, further comprising a housing in which the motor, the liquid medicine container and the plunger are housed.

13. The liquid medicine administration device according to claim 12, further comprising an attachment portion attached to a distal end portion of the liquid medicine container and protruding outside the housing in a direction away from the housing, the attachment portion being configured to be connected to a tube of an administration tool that is used to administer the liquid medicine to a living body.

14. The liquid medicine administration device according to claim 12, further comprising a battery positioned in the housing and connected to the motor to supply the current to the motor.

15. A method comprising:
  inserting a needle tube into a living body, the needle tube being connected to an opening at a distal end of a liquid medicine container containing liquid medicine, with a gasket positioned in the liquid medicine container and connected to a plunger so that axial movement of the plunger results in axial movement of the gasket, the plunger being operatively connected to a motor so that operation of the motor results in the axial movement of the plunger and the gasket, the motor rotating during operation, and rotation of the motor being detected by a rotation detection unit;
  starting the motor;
  operating the motor after the starting of the motor so that the motor rotates and axially moves the plunger and the gasket toward the distal end of the liquid medicine container to discharge the liquid medicine through the opening at the distal end of the liquid medicine container and is delivered to the needle tube so that the liquid medicine is administered to the living body;
  starting the rotation detection unit after the starting of the motor and after the operating of the motor; and operating the rotation detection unit after the starting of the rotation detection unit so that the rotation detection unit detects the rotation of the motor.

16. The method according to claim 15, wherein the starting of the operation of the rotation detection unit after the motor is operating comprises starting the operation of the rotation detection unit after current supplied to the motor is stabilized.

17. The method according to claim 15, wherein the rotation detection unit is an encoder including a photointerrupter.

18. The method according to claim 15, further comprising a power supply that supplies current to the motor and to the rotation detection unit, the starting of the operation of the rotation detection unit after the motor is operating reducing a load on the power supply at the starting of the operation of the motor.

19. The method according to claim 15, further comprising a battery that supplies current to the motor and to the rotation detection unit, the starting of the operation of the rotation detection unit after the motor is operating reducing a load on the battery at the starting of the operation of the motor.

* * * * *